(12) United States Patent
Fabbri

(10) Patent No.: US 8,242,265 B2
(45) Date of Patent: Aug. 14, 2012

(54) PURIFICATION PROCESS COMPRISING DISSOLVING AN ORGANIC COMPOUND IN CARBONATED WATER AND FREEZE-DRYING

(75) Inventor: Oliver Jean Fabbri, London (GB)

(73) Assignee: Texcontor Etablissement, Vuduz (LI)

( * ) Notice: Subject to any disclaimer, the term of this patent is extended or adjusted under 35 U.S.C. 154(b) by 387 days.

(21) Appl. No.: 12/522,312

(22) PCT Filed: Jan. 14, 2008

(86) PCT No.: PCT/GB2008/000108
§ 371 (c)(1),
(2), (4) Date: Nov. 30, 2009

(87) PCT Pub. No.: WO2008/087383
PCT Pub. Date: Jul. 24, 2008

(65) Prior Publication Data
US 2010/0105892 A1  Apr. 29, 2010

(30) Foreign Application Priority Data
Jan. 17, 2007  (GB) .................................. 0700878.2

(51) Int. Cl.
*C07D 413/08* (2006.01)
*C07B 63/00* (2006.01)

(52) U.S. Cl. ........................................................ 540/596
(58) Field of Classification Search .................... 540/96
See application file for complete search history.

(56) References Cited

U.S. PATENT DOCUMENTS

| | | |
|---|---|---|
| 3,288,820 A | 11/1966 | Argoudelis et al. |
| 4,894,369 A | 1/1990 | Sleigh et al. |
| 5,593,983 A | 1/1997 | Campbell |
| 5,817,803 A | 10/1998 | Magni et al. |
| 6,090,957 A | 7/2000 | Magni et al. |
| 2003/0115687 A1 | 6/2003 | Belcour-Castro et al. |
| 2005/0159398 A1 | 7/2005 | Adar et al. |
| 2006/0009485 A1 | 1/2006 | Friedman et al. |
| 2006/0058275 A1 | 3/2006 | Friedman et al. |
| 2006/0058276 A1 | 3/2006 | Friedman et al. |
| 2007/0265237 A1 | 11/2007 | Mendez et al. |

OTHER PUBLICATIONS

International Search Report for PCT/GB2008/000108 mailed Apr. 23, 2008.
Database WPI, Section Ch, Week 200733, Accession No. 2007-344681 [33], Fu, Y. et al., "Stabilised Lyophilise Preparation Bromide" & CN 1864667, Chongqing Pharm Res Inst 6 Ltd., (Nov. 22, 2006), Abstract.

*Primary Examiner* — Brenda Coleman
(74) *Attorney, Agent, or Firm* — Nixon & Vanderhye P.C.

(57) ABSTRACT

A process for the purification of a crude organic compound comprising dissolving said compound in carbonated water to form a solution and freeze drying said solution.

7 Claims, No Drawings

PURIFICATION PROCESS COMPRISING DISSOLVING AN ORGANIC COMPOUND IN CARBONATED WATER AND FREEZE-DRYING

This application is the U.S. national phase of International Application No. PCT/GB2008/000108 filed 14 Jan. 2008, which designated the U.S. and claims priority to GB Application No. 0700878.2 filed 17 Jan. 2007, the entire contents of each of which are hereby incorporated by reference.

This invention relates to a process for the purification of organic chemical compounds, especially certain neuromuscular blocking agents, in particular rocuronium bromide, by freeze drying the compound from a carbonated aqueous solution.

Neuromuscular blocking agents are muscle-relaxing drugs which possess muscle paralyzing activity. These agents are known to interrupt transmission of nerve impulses at the skeletal neuromuscular junction and cause skeletal muscle contraction to cease.

Neuromuscular blocking agents are routinely used in anaesthesia, for example, to enable endotracheal intubation and to facilitate mechanical ventilation, e.g. relaxation of vocal cords, jaw muscles etc, to facilitate surgery, e.g. providing generalized muscle relaxation so as to allow surgical access to body cavities, in particular the abdomen and thorax, without hindrance from voluntary or reflex muscle movement. The agents also prevent the violent muscle movements associated with electroconvulsive therapy treatment and surgery under convulsive conditions. Typically, administration is performed intravenously by injection of a suitable dosage form.

Most of the clinically-used neuromuscular blocking agents are "non-depolarizing" and these include tubocurarine, atracurium, (cis)atracurium, mivacurium, pancuronium, vecuronium, rapacuronium and rocuronium. Non-depolarizing neuromuscular blocking agents compete with acetylcholine for binding to muscle nAChRs, but unlike depolarizing neuromuscular blocking agents, they do not activate the channel. Rather, non-depolarizing neuromuscular blocking agents block the activation of the channel by acetylcholine and hence prevent cell membrane depolarization, and, as a result, the muscle becomes flaccid.

1-[(2.beta.,3.alpha.,5.alpha.,16.beta.,17.beta.)-17-acetoxy-3-hydroxy-2-(4-morpholinyl)-androstan-16-yl-]-1-(2-propenyl)pyrrolidinium bromide, also known by the name rocuronium bromide, is a neuromuscular blocking agent having a steroidal skeleton as shown below:

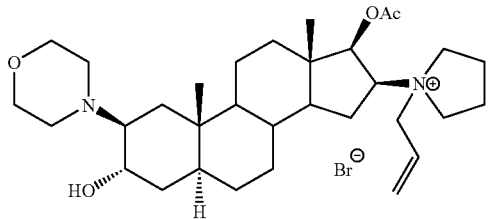

Rocuronium bromide, which is presently marketed in the North America under the brand name Zemuron.RTM, and elsewhere under the brand name Esmeron.RTM., has been used in clinical practice since 1994 as a non-depolarizing neuromuscular blocking agent. It is known for its remarkably rapid yet controllable onset, depending on dose and intermediate duration. Rocuronium bromide is indicated for patients as an adjunct to general anesthesia, to facilitate both rapid sequence and routine tracheal intubation, and to provide skeletal muscle relaxation during surgery or mechanical ventilation.

The art is replete with differing syntheses of rocuronium bromide such as U.S. Pat. No. 5,808,051. However, whilst rocuronium bromide is a simple compound to synthesise, it is a very difficult compound to purify. Organic chemists are armed with various standard purification techniques for the isolation of highly pure target materials. Chromatography is often used but is generally impractical on a large scale and is associated with low product yields.

Perhaps the most commonly employed technique is recrystallisation where the target material is crystallised out of a mixture of solvent and antisolvent. US 2006/0058276 describes a process for the preparation and purification of rocuronium bromide in which a recrystallisation process is employed.

Whilst this technique is applicable to rocuronium bromide, the compound tends to form solvates with the solvents employed in recrystallisation. The pharmaceutical chemist does not however want his rocuronium bromide in the form of a solvate. Moreover, residual solvent levels are unacceptably high. Recrystallisation is not therefore an ideal technique to use in this case.

Another commonly used technique for purifying an active agent is lyophilisation however, when rocuronium bromide dissolves in water, a solution of basic pH is formed and the compound is highly unstable in a basic aqueous solution so this technique cannot be used. US 2006/0058275 suggests buffering the aqueous solution to prevent the formation of a basic pH. Sodium acetate is their preferred buffer. Unfortunately however, when the buffered solution is freeze dried, the resulting solid contains unacceptable amounts of buffer.

In a search for further purification techniques, US 2006/0009485 suggests the radical step of dealkylating the rocuronium bromide, purifying the dealkylated product before converting it back to the alkylated bromide. This process is obviously complex, costly and time consuming and there remains therefore a need to devise other purification techniques for obtaining rocuronium bromide in a highly pure form, in particular with low residual solvent levels, which do not lead to high levels of residual buffer or solvate formation or involve complex product manipulation processes.

The present inventors have surprisingly found that rocuronium bromide can be prepared with very low levels of residual solvent and without buffer contamination and without complex dealkylation procedures if the rocuronium bromide is dissolved in a carbonated aqueous solution and then freeze dried. During the freeze drying process, the carbon dioxide is eliminated leaving a highly pure active compound in which solvent levels are very low. Whilst the inventors have devised this technique for the elimination of residual solvents from rocuronium bromide, it will be appreciated that it is generally applicable to the isolation of any appropriate organic chemical compound, in particular those which are unstable in basic solution or those which are difficult to purify by other techniques such as recrystallisation, e.g. due to solvate formation.

Thus, viewed from one aspect, the invention provides a process for the purification of a crude organic compound comprising dissolving said compound in carbonated water to form a solution and freeze drying said solution.

Alternatively viewed, the invention provides a process for reducing or eliminating residual solvent in a crude organic compound containing at least one residual solvent comprising dissolving said compound in carbonated water to form a solution and freeze drying said solution.

Viewed from another aspect the invention provides rocuronium bromide obtained by the process as herein before defined.

Viewed from another aspect the invention provides use of carbonated water as a solvent for freeze drying.

The present invention relates to a process for purifying an organic compound, in particular, a synthetic organic compound such as a pharmaceutical compound. During the synthesis or isolation of an organic compound, it is almost inevitable that the desired compound is isolated along with a solvent or mixture of solvents. Whilst normal work up procedures and subsequent standard purification techniques often remove most solvent traces, for certain applications, residual solvent levels must be exceedingly low and hence purity very high and some compounds isolated after these procedures still need further purification to reduce solvent levels. The process of the invention seeks to reduce or eliminate residual solvents from a crude organic compound starting material. The solvents may be present in the starting material in the form of a solvate with the organic compound or present in their natural solvent form.

Thus, the term "purification" as used herein means the reduction or elimination of residual solvent(s). A crude organic compound is one in which at least one solvent is present, either in the form of a solvate with the compound or as a solvent itself.

The compound which is purified using the process of the invention is one which is in crude form, e.g. it is in a form isolated after reaction work up but before conventional purification steps are carried out, e.g. before recrystallisation.

The process is however, also suitable for purifying still further compounds, such as rocuronium bromide, which may have been subjected to recrystallisation or other conventional purification techniques but still contain unacceptable levels of residual solvents, e.g. in the form of solvates of the organic compound being purified.

It will be clear therefore that the process acts on an impure starting material, i.e. one containing an amount of at least one residual solvent.

The amount of residual solvent present at the start of the process of the invention can vary over a wide range and will depend on the nature of the starting material. A crude organic compound starting material derived straight from a work up procedure is likely to contain higher levels of solvent than one which is derived from a recrystallisation procedure. What is critical is that the process of the invention allows a reduction in the level of solvent present to occur.

The percentage reduction may be at least 10%, preferably at least 50%, especially at least 100%. Ideally the solvent level (in wt %) after the process of the invention will be less than 1000 ppm, preferably less than 750 ppm, more preferably less than 500 ppm, especially less than 300 ppm.

The amount of solvent in the crude organic compound starting material may be as high as 1 wt %, preferably as high as 5 wt %, more preferably as high as 10 wt %, especially as high as 15 wt %.

Solvents which might be present and hence removed during the process of the invention can be any organic solvent conventionally used in the art. All manner of organic solvents are known in the art and can be removed using the process of the invention. It is required however, that a solution is formed when the crude organic compound (containing the solvent to be removed) is dissolved in the carbonated water. The word "solution" is used herein to specify that after dissolution a one phase system forms, i.e. there can be no organic phase present.

Whilst it is obvious that water soluble solvents such as alcohols will form the necessary one phase system, it will also be appreciated by the skilled man that sparingly water soluble solvents are also capable of forming a one phase aqueous solution as required of the invention as the amount of solvent to be dissolved is low. There is a considerable excess of water allowing many solvents to form the desired one phase system.

As the quantity of solvent in the crude product is typically less than 15 wt % and, for example, the crude organic compound might be dissolved in 6 times its weight of water, the amount of solvent may be of the order of 2.5 g/L of water. As it is only this small amount of solvent which needs to dissolve to form the one phase system with the carbonated water, many solvents can be removed by the process of the invention. A solvent such as dichloromethane, which is immiscible with water at very high concentration is miscible with water in low concentration so is still capable of forming a one phase system.

Thus, to remove nominally water miscible solvents might require the addition of less water than to remove a nominally sparingly water soluble solvent. The person skilled in the art can however, add sufficient water to ensure that a one phase system results for any desired solvent.

The water solubility of the solvent may therefore be at least 1 g/L of water, preferably at least 2.5 g/L, especially at least 10 g/L of water.

It is preferred, if the solvent is a polar solvent, preferably water miscible solvent, especially a water soluble solvent. Polar solvents which can be removed include alcohols (e.g. aliphatic or aryl alcohols), polyols, esters, halogenated solvents, ethers, cyanides/nitriles, ketones, aldehydes, amines, amides, formamides, sulphides, sulphoxides and carboxylic acids. Specific solvents which can be removed include dimethylformamide (DMF), DMSO, THF, acetone, dichloromethane (DCM), chloroform, methyl-tert-butylether (MTBE), diethylether, acetic acid, acetonitrile, methanol, ethanol, diglyme, pyridine, and ethyl acetate. It is also possible of course to reduce the level of solvent mixtures in a starting material.

The nature of the compound purified by the process of the invention can vary widely. It is believed that the use of carbonated water as a solvent from which to freeze dry an organic compound to improve its purity, in particular to reduce solvent levels, is new and the technique can therefore be applied to all manner of compounds. It is essential however, that the compound to be purified dissolves in water to form a solution for the process of the invention to be effective. The solubility of chemical compounds can vary with pH and it is preferred if the compound being purified is water soluble at neutral pH. The water solubility of the organic compound is preferably at least 10 g/L of water. Preferably at least 100 g of the compound will dissolve in 1 L of water. Most preferably, the compound is at least water soluble at pH's of from 4 to 8. In addition it is also preferably stable at pH from 4 to 8 and optionally unstable at pH>8.

Certain chemical compounds are of course more obviously able to benefit from the process of the invention. In particular, high purity, especially low residual solvent levels, is a feature primarily associated with compounds for use as pharmaceuticals so the compound used in the process of the invention is preferably a pharmaceutical.

The process of the invention is also one which is most advantageously carried out on a compound which cannot be purified by other more conventional techniques such as recrystallisation, e.g. due to the formation of solvates. The process is also preferably carried out on a compound which forms a basic solution of pH greater than 8 on dissolution in water. It is also preferred if the chemical compound being purified is one which is stable in water at a pH of less than 8, e.g. 4-8.

The compound to be purified is preferably a salt, especially an ammonium salt and/or halide salt. Mixtures of compounds could also be purified by this technique, e.g. mixtures of salts or mixtures of a salt and a non salt compound.

Suitable compounds for purification using the claimed process therefore include peptides, amino acids, proteins, steroids, polycyclic compounds. Preferably, the compound is a pharmaceutical, in particular a relatively small pharmaceutical (e.g. one molecular weight (Mw) of less than 1000, preferably less than 750, e.g. Mw 100 to 700).

In a highly preferred embodiment, the compound is a neuromuscular blocking agent e.g. one based on tubocurarine, atracurium, (cis)atracurium, mivacurium, pancuronium, vecuronium, rapacuronium and rocuronium (e.g. salts thereof). More specifically the compound is tubocurarine chloride, atracurium besylate, pancuronium bromide, vecuronium bromide, and rocuronium bromide. Most preferably the compound is a rocuronium salt such as rocuronium bromide.

The water used to form the carbonated water solvent should itself be as pure as possible. Thus purified water should be employed. This should then be carbonated e.g. by bubbling carbon dioxide through the water. The amount of carbonation required can vary and it is possible to use water saturated with carbon dioxide. Preferably however, the amount of carbonation required is measured through the pH of the carbonated water. Preferably therefore, the carbonated water, prior to dissolution of the chemical compound therein, should be carbonated so as to ensure that the pH of the carbonated water is less than 6, preferably less than 5.5, more preferably less than 5, especially less than 4.5.

Preferably, the pH of the carbonated water should be kept above 4.

The crude organic compound can then be dissolved in the carbonated water. To aid dissolution, any technique such as stirring or sonication could be used at this point. It would also be possible to gently heat the solution to encourage dissolution as long as the compound in question was not heat sensitive. Preferably however, the carbonated water is kept cool, e.g. less than 10° C. This may prevent degradation of the compound. For example, the acetate of rocuronium bromide hydrolyses when it is solved in water at a higher temperature. The aim during dissolution is to achieve complete dissolution of the chemical compound in the carbonated water.

The relative amounts of carbonated water to organic compound are not critical although a balance must be struck between too little water for dissolution to readily occur and too much water meaning a lot of water needs to be removed during freeze drying. A suitable weight ratio of compound to carbonated water is 1:20 to 1:3, preferably 1:15 to 1:5, e.g. 1:10. Thus, there should be, for example, 10 times more weight of water than material being dissolved in the water. These ratios apply to the weight of material added to the water, i.e. the weight of the crude compound.

During or after dissolution it may be necessary to further carbonate the water. The compound dissolved may well be basic and may have raised the pH of the carbonated water. Some carbonation may also have been lost through escape of carbon dioxide to the air during the dissolution phase. It is preferred if the freeze drying step occurs from a solution whose pH is no more than 8. Thus, it may be necessary to add more carbon dioxide to the solution after dissolution, but preferably during dissolution, to prevent pH rising above 8.

Some chemical compounds may be pH sensitive and may not tolerate basic pH's. In this scenario, the skilled man needs to carefully monitor pH during the dissolution phase to ensure that enough $CO_2$ is added to the water to compensate for any increase in pH caused by the dissolution of the compound.

The solution can then be freeze dried using conventional techniques. Thus, the solution can be charged to the freeze drier and frozen over a short period of time, e.g. 1 to 10 hours, preferably less than 5 hours. Once frozen, the vacuum can be connected and the drier heated e.g. up to 15° C. Once the water has been removed, the solid product can be isolated in very high purity, e.g. at least 99% purity, especially at least 99.5% purity, e.g. 99.9% purity or higher.

Thus, viewed from a further aspect the invention provides a process for the purification of a crude organic compound comprising:
(I) dissolving said compound in carbonated water having a pH of less than 6 to form a solution; and
(II) freeze drying said solution.

More particularly, the invention provides a process for the purification of a crude organic compound comprising:
(I) dissolving said compound in carbonated water having a pH of less than 6 to form a solution;
(II) during and/or after dissolution further carbonating the water to maintain or restore a pH of less than 8; and
(III) freeze drying said solution.

Once the compound has been dissolved in the carbonated water solution, but prior to freeze drying, it may be preferable to carry out an intermediate solvent removal step in which any residual solvents present in the crude material dissolved in the carbonated water are reduced. This may be particularly important where the amount of solvent in the starting material is particularly high, e.g. greater than 10 wt %. This can be achieved using vacuum distillation. Again, during this process pH should be monitored to ensure that the pH of the solution does not increase above 8 as residual solvent(s) is removed. Further carbonation can be carried out to prevent this occurring if necessary.

Thus, viewed from another aspect the invention provides a process for the purification of a crude organic compound comprising:
(I) dissolving said compound in carbonated water having a pH of less than 6 to form a solution; optionally
(II) during and/or after dissolution further carbonating the water to maintain or restore a pH of less than 8;
(III) carrying out an intermediate solvent removal step in which residual solvent present in the crude material dissolved in the carbonated water is reduced, e.g. a vacuum distillation step; and
(IV) freeze drying said solution.

It may also be necessary to filter the carbonated water solution prior to freeze drying to remove any non soluble impurities which may have been present in the crude organic compound starting material initially added to the carbonated water.

The purified chemical compound obtained using the process of the invention, i.e. after freeze drying can then be formulated as is well known in the art. Typically, it will be formulated as a pharmaceutical composition along with any conventional pharmaceutical excipients. Such a composition could be in any conventional dosage form such as a powder, tablet, capsule, pill, injectable solution etc.

The invention will now be described further with reference to the following non limiting examples.

EXAMPLE 1

Synthesis of Rocuronium Bromide

Rocuronium bromide was synthesised using conventional chemistry from the reaction of 1.7 kg of Rocuronium and 1.21 L of allyl bromide in 17 L of DCM.

After 8 hours at reflux the reaction was worked up using conventional procedures to form a wet solid. The solvents used in work up were DCM and MTBE. The amounts of these solvents in the wet solid formed after work up are given in Table 1 below.

EXAMPLE 2

Freeze Drying

Purified water (12 L) was cooled to 5° C. and carbon dioxide bubbled until the pH was lower than 4,5. The wet product of example 1 was charged and carbon dioxide gas bubbled again until a pH lower than 8 was achieved.

When the solid was completely dissolved, vacuum was connected and the solution kept at 5±3° C. until the level of MTBE was lower than 900 ppm, bubbling carbon dioxide when the pH is higher than 8. The solution was unloaded through a 0,45 μm filter rinsing the reactor with purified water.

The aqueous solution of the product was charged in a freeze-dryer with shelves previously cooled at 1° C. This solution was frozen during approximately 4 hours. Once the solution was completely frozen, the vacuum was connected (0,10-0,15 mbar) and the shelves heated at 15° C. during 26 h. The solid was unloaded when the humidity of the surrounding area is lower than 35% and the temperature below 30° C.

The yield was 1,8 kg (about 84%). PURITY≧99.5%
Solvent Levels

The amount of MTBE and DCM were determined after each stage of the process and results are presented below.

| Solvent | Wet solid | After freeze-drying |
|---------|-----------|---------------------|
| MTBE | 12% (wet solid) | 250 ppm |
| DCM | None detected | None detected |

The process of the invention therefore enables the reduction of residual solvent from a crude organic compound.

The invention claimed is:

1. A process for the purification of rocuronium bromide comprising dissolving said compound in carbonated water to form a solution and freeze drying said solution.

2. A process for reducing or eliminating residual solvent in rocuronium bromide containing at least one residual solvent comprising dissolving said compound in carbonated water to form a solution and freeze drying said solution.

3. A process as claimed in claim 1 wherein the carbonated water has a pH of less than 6 prior to dissolution.

4. A process for the purification of rocuronium bromide as claimed in claim 1 comprising:
   (I) dissolving said compound in carbonated water having a pH of less than 6 to form a solution; and
   (II) freeze drying said solution.

5. A process as claimed in claim 4 comprising:
   (I) dissolving said compound in carbonated water having a pH of less than 6 to form a solution;
   (II) during and/or after dissolution further carbonating the water to maintain or restore a pH of less than 8; and
   (III) freeze drying said solution.

6. A process as claimed in claim 4 comprising:
   (I) dissolving said compound in carbonated water having a pH of less than 6 to form a solution; optionally
   (II) during and/or after dissolution further carbonating the water to maintain or restore a pH of less than 8;
   (III) carrying out an intermediate solvent removal step in which residual solvent present in the crude material dissolved in the carbonated water is reduced; and
   (IV) freeze drying said solution.

7. A process as claimed in claim 6, wherein in step (III) the crude material dissolved in the carbonated water is reduced in a vacuum distillation step.

\* \* \* \* \*